US011547117B2

(12) United States Patent
Seal et al.

(10) Patent No.: US 11,547,117 B2
(45) Date of Patent: Jan. 10, 2023

(54) COATING FOR CAPTURING AND KILLING VIRUSES ON SURFACES

(71) Applicant: UNIVERSITY OF CENTRAL FLORIDA RESEARCH FOUNDATION, INC., Orlando, FL (US)

(72) Inventors: Sudipta Seal, Orlando, FL (US); Craig Neal, Orlando, FL (US); Udit Kumar, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 17 days.

(21) Appl. No.: 17/235,827

(22) Filed: Apr. 20, 2021

(65) Prior Publication Data
US 2021/0321618 A1 Oct. 21, 2021

Related U.S. Application Data

(60) Provisional application No. 63/012,595, filed on Apr. 20, 2020.

(51) Int. Cl.
A01N 59/16 (2006.01)
A01N 25/10 (2006.01)
A01N 25/24 (2006.01)

(52) U.S. Cl.
CPC ............. A01N 59/16 (2013.01); A01N 25/10 (2013.01); A01N 25/24 (2013.01); A61L 2420/08 (2013.01)

(58) Field of Classification Search
CPC ...................... A01N 59/16; A61L 2420/08
See application file for complete search history.

(56) References Cited

FOREIGN PATENT DOCUMENTS

WO WO-2011151385 A1 * 12/2011 ............. A61L 27/34

OTHER PUBLICATIONS

Kumar, Udit et al., "Potent Inactivation of Human Respiratory Viruses Including SARS-CoV-2 by a Photoactivated Self-Cleaning Regenerative Antiviral Coating", ACS Appl. Mater. Interfaces, 2022, 15 pages, https://doi.org/10.1021/acsami.2c11653.
Babu, Suresh et al., "Multicolored redox active upconverter cerium oxide nanoparticle for bio-imaging and therapeutics", Chem. Commun., 2010, 46, 6915-6917.
Baloh, Jure et al., "Healthcare Workers' Strategies for Doffing Personal Protective Equipment", Clinical Infectious Diseases, 2019;69(S3):S192-S198.
Bracey, Daniel et al., "A porcine xenograft-derived bone scaffold is a biocompatible bone graft substitute: An assessment of cytocompatibility and the alpha-Gal epitope", Xenotransplantation, 2019, 26:e12534, 11 pages.
Cates, Ezra L. et al., "Converting Visible Light into UVC: Microbial Inactivation by Pr3+—Activated Upconversion Materials", Environ. Sci. Technol. 2011, 45, 3680-3686.
Cates, Ezra L. et al., "Delineating Mechanisms of Upconversion Enhancement by Li+ Codoping in Y2SiO5Pr3+", J. Phys. Chem. C 2012, 116, 12772-12778.
Cates, Ezra L. et al., "Upconversion under polychromatic excitation: Y2SiO5:Pr3+, Li+ converts violet, cyan, green, and yellow light into UVC", Optical Materials 35 (2013) 2347-2351.
Cates, Ezra L. et al., "Visible-to-UVC upconversion efficiency and mechanisms of Lu7O6F9: Pr3p and Y2SiO5:Pr3p ceramics". Journal of Luminescence 160 (2015) 202-209.
Zhang, Wenyan et al., "Visible-to-ultraviolet Upconvertion: Energy transfer, material matrix, and synthesis strategies", Applied Catalysis B: Environmental 206 (2017) 89-103.
Cates, Stephanie L. et al., "Synthesis and Characterization of Visible-to-UVC Upconversion Antimicrobial Ceramics", Environmental science & technology, 2014, 48(4): p. 2290-2297.
CDC, "Cleaning and Disinfecting Your Home", https://www.cdc.gov/coronavirus/2019-ncov/prevent-getting-sick/disinfecting-your-home.html?CDC_AA_refVal=https%3A%2F%2Fwww.cdc.gov%2Fcoronavirus%2F2019-ncov%2Fprevent-getting-sick%2Fcleaning-disinfection.html, Downloaded off Internet Sep. 9, 2021, 5 pages, 2019.
Chang, Jinfa et al., "Stable Fe2P2S6 Nanocrystal Catalyst for High-Efficiency Water Electrolysis", Small Methods 2020, 4, 1900632, 7 pages.
Chen, Guanying et al., "Upconversion Nanoparticles: Design, Nanochemistry, and Applications in Theranostics", Chem. Rev. 2014, 114, 5161-5214.
Cruz, Maria A. et al., "La Crosse Virus Infection of Human Keratinocytes Leads to Interferon-Dependent Apoptosis of Bystander Non-Infected Cells In Vitro", Viruses 2020, 12, 253; doi:10.3390/v12030253.
Deshpande, Sameer et al., "Size dependency variation in lattice parameter and valency states in nanocrystalline cerium oxide", Appl. Phys. Lett. 87, 133113 (2005); htpps://doi.org/10.1063/1.2061873.
Fox, Candace R. et al., "Histone Deacetylase Inhibitors Enhance Cell Killing and Block Interferon-Beta Synthesis Elicited by Infection with an Oncolytic Parainfluenza Virus", Viruses 2019, 11, 431; doi:10.3390/v11050431.

(Continued)

Primary Examiner — Kyle A Purdy
(74) Attorney, Agent, or Firm — Timothy H. Van Dyke; Wolter, Van Dyke, Davis, Pllc.

(57) ABSTRACT

Disclosed herein is a nano-coating platform that is designed to 'capture' and 'kill' (i.e. inactivate) virus species to prevent surface to surface contamination/transmission and thereby the spread of novel viruses. The platform is comprised of alternating layers of charged polymers (producing a multilayer coating). The cationic layer may be grafted with oligomeric species, chosen to bind strongly to unique/specific virus surface features, thereby mediating capture of the virus (with the choice of oligomeric species allowing generalization to a given virus). Natural light (excitation) to UV (local emission) up-converting nanoparticles are seeded into the anionic layer and mediate the inactivation ('killing') of the bound virus species.

19 Claims, 2 Drawing Sheets

(56) References Cited

OTHER PUBLICATIONS

Galindo, C. et al., "UV-H2O2 oxidation of monoazo dyes in aqueous media: a kinetic study", Dyes and Pigments, 40 (1998)27-35.
Gao, Wei et al., "A twopronged strategy to enhance visiblelightdriven overall water splitting via visibletoultraviolet upconversion coupling with hydrogenoxygen recombination inhibition", Applied Catalysis B: Environmental 212 (2017) 23-31.
Gupta, Ankur et al., "Antioxidant properties of ALD grown nanoceria films with tunable valency", Biomater. Sci., 2019, 7, 3051.
Hindawi, Salwa I. et al., "Inactivation of Middle East respiratory syndrome-coronavirus in human plasma using amotosalen and ultraviolet A light", TRANSFUSION vol. 58, Jan. 2018, 52-59.
Hu, Changhong et al., "Visible-to-ultraviolet upconversion in Pr3+:Y2SiO5 crystals", Chemical Physics 325 (2006) 563-566.
Jeyaranjan, Aadithya et al., "Scalable ternary hierarchical microspheres composed of PANI/ rGO/CeO2 for high performance supercapacitor applications", Carbon 151 (2019) 192e202.
Johnson, John B. et al., "Interactions of Human Complement with Virus Particles Containing the Nipah Virus Glycoproteins", Journal of Virology, Jun. 2011, p. 5940-5948.
Ju, Licheng et al., "Significantly Improved Cyclability of Conversion-Type Transition Metal Oxyfluoride Cathodes by Homologous Passivation Layer Reconstruction", Adv. Energy Mater. 2020, 10, 1903333, 8 pages.
Li, Siwen et al., "Dual antibacterial activities of a chitosan-modified upconversion photodynamic therapy system against drug-resistant bacteria in deep tissue", Nanoscale, 2017, 9, 3912-3924.
Lim, Meng Earn et al., "Photodynamic inactivation of viruses using upconversion nanoparticles", Biomaterials 33 (2012) 1912e1920.
McCarthy, Niall, "Confirmed Covid-19 Cases in the U.S.", Https:// www.statista.com/chart/20978/coronavirus-cases-us-map/, Apr. 26, 2021, 4 pages.
Medical Devise Network, "WHO urges increased production of personal protective equipment", https://www.medicaldevice-network.com/news/who-personal-protective-equipment/, Mar. 4, 2020, 5 pages.
Neal, Craig J. et al., "Metal-Mediated Nanoscale Cerium Oxide Inactivates Human Coronavirus and Rhinovirus by Surface Disruption", https://doi.org/10.1021/acsnano.1c04142, 2021, 13 pages.
Phan, Linh T. PhD. et al., "Respiratory viruses on personal protective equipment and bodies of healthcare workers", Infection Control & Hospital Epidemiology (2019), 40, 1356-1360.
Sahu, Sushant P. et al., "The Myth of Visible Light Photocatalysis Using Lanthanide Upconversion Materials", Environ. Sci. Technol. 2018, 52, 2973-2980.
Saraf, Nileshi et al., "Microsensor for limonin detection: An indicator of citrus greening disease", Sensors & Actuators B. Chemical 283 (2019) 724-730.
Schnirring, Lisa et al., "WHO warns of COVID-19-related protective equipment shortage", https://www.cidrap.umn.edu/news-perspective/2020/03/who-warns-covid-19-related-protective-equipment-shortage, Mar. 3, 2020, 4 pages.
Sener, Gulsu et al., "Injectable, self-healable zwitterionic cryogels with sustained microRNA—cerium oxide nanoparticle release promote accelerated wound healing", Acta Biomaterialia 101 (2020) 262-272.
Shultz, L.R. et al., "A Broader-scope Analysis of the Catalytic Reduction of Nitrophenols and Azo Dyes with Nobel Metal Nanoparticles", ChemCatChem 2019, 11, 2590-2595.
Singh, Virendra et al., "A facile synthesis of PLGA encapsulated cerium oxide nanoparticles: release kinetics and biological activity", Nanoscale, 2012, 4, 2597.
Szeto, Wai et al., "The efficacy of vacuum-ultraviolet light disinfection of some common environmental pathogens", BMC Infectious Diseases, (2020) 20:127, 9 pages.
Van Doremalen, Neeltje et al., Aerosol and surface stability of HCoV-19 (SARS-CoV-2) compared to SARS-CoV-1, (SARS-CoV-2) compared to SARS-CoV-1. medRxiv, 2020.
Wang, Guanzhi et al., "Programmable Exposure of Pt Active Facets for Efficient Oxygen Reduction", Angew. Chem. Int. Ed. 2019, 58, 15848-15854.
WHO, "Coronavirus disease 2019 (COVID-19) Situation Report-45", https://www.who.int/emergencies/diseases/novel-coronavirus-2019/technicalguidance/ laboratory-guidance, Mar. 5, 2020, 10 pages.
WHO, "Infection prevention and control during health care when coronavirus disease (COVID-19) is suspected or confirmed: Interim guidance", WHO/2019-nCoV/IPC/2021.1, 2021, 23 pages.
Wikipedia, "COVID-19 pandemic", https://en.wikipedia.org/w/index.phptitle=COVID-19_pandemic&oldid=1043360818, Sep. 9, 2021, 104 pages.

* cited by examiner

COATING FOR CAPTURING AND KILLING VIRUSES ON SURFACES

BACKGROUND

The WHO has recently declared the COVID-19/novel coronavirus (CoV) outbreak a pandemic (>170,000 infected, >7000 deaths globally; In USA, >8000 cases, >150 deaths, & increasing): posing a threat to human well-being. While there are detection and diagnostics available, there is an urgent need for better personal protective equipment (PPE; nitrile gloves, face masks, gowns & other surfaces) which represent the front line of defense for health workers, first responders, and the general population. However, they typically provide only moderate protection in their current form: functioning only as a physical barrier to infection. Ideally, future PPE products will be modified with functional nanomaterials to limit surface-to-surface contamination.

DETAILED DESCRIPTION

Disclosed herein is a nano-coating platform that is designed to 'capture' and 'kill' (i.e. inactivate) virus species to prevent surface to surface contamination/transmission and thereby the spread of novel viruses. The platform is comprised of alternating layers of charged polymers (producing a multi-layer coating). The cationic layer may be grafted with oligomeric species, chosen to bind strongly to unique/specific virus surface features, thereby mediating capture of the virus (with the choice of oligomeric species allowing generalization to a given virus). Natural light (excitation) to UV (local emission) up-converting nanoparticles are seeded into the anionic layer and mediate the inactivation ('killing') of the bound virus species. Binding of virus to the coating surface layer can reduce interaction with sub-layers and allow release of inactivated bound virus: producing a fresh surface to allow further virus capture if sufficiently soiled.

Overview

Figure 1:
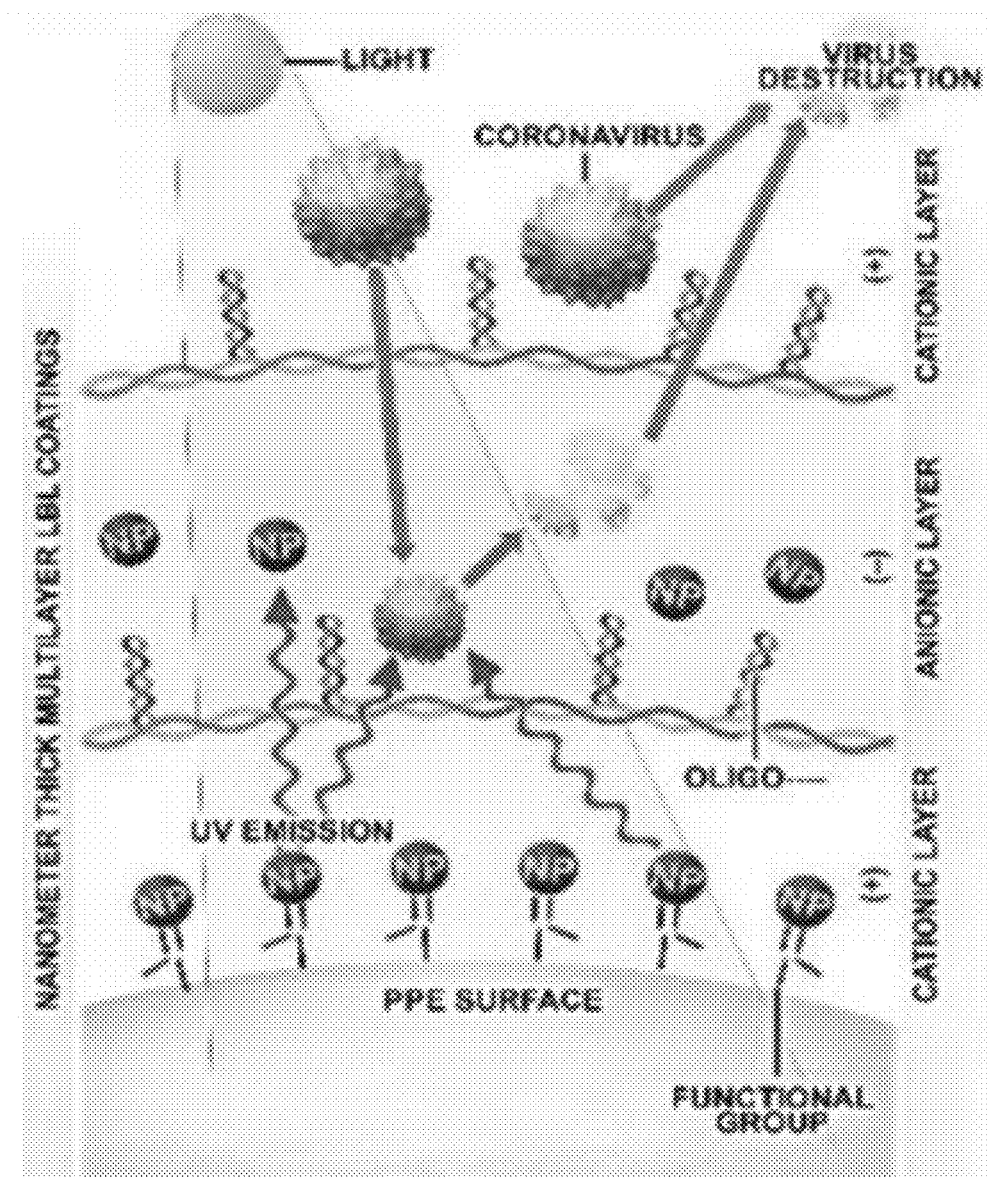
FIG. 1 shows a diagram depicting a coating construct embodiment for capturing and killing viruses.

The current emergency requirement is to obtain primary protection from COVID-19/SARS CoV2 coronavirus (CoV) strain. CoV leads to severe acute respiratory disease resulting in death. Current Statistics: The world health organization (WHO) declared >170,000 people have been infected and 7000 reported deaths worldwide by CoV since the first identified case in China (December 2019) [1-4]. It is assumed that the infection is via surface-to surface contamination and person-to-person spread. Challenge & Importance of PPE: The health workers and first responders rely on personal protective equipment (PPE) to protect themselves from infection. In the current situation, PPE is the only way to control the spreading and prevent CoV infection [5, 6]. Currently, there is a huge shortage in the supply of PPE (gloves, masks, gowns, etc.) in USA and increasing daily. Demand has further increased due to the suggestion by WHO to use PPE and persistent use of PPE by not-at-risk individuals. [7] The U.S. government and industries are offering incentives to increase production of medical supplies including PPEs. [8] In a CNN podcast, Alex Azar, USA HHS (Health Human Services) Secretary, recently stated, "We will be increasing the much-needed PPE to combat the COVID-19 outbreak" Most importantly, PPE typically provides only moderate protection and doesn't kill the virus, resulting in contamination that can transmit CoV to others. [9] A recent unpublished study showed that COVID-19 survives on copper, stainless steel and plastic surfaces for up to 4, 48 and 72 hrs, respectively, [10] allowing easy vectored contamination by surface to surface contact. Ideally, future PPE products should be modified with functional nanomaterials to limit surface-to-surface contamination by inactivating the virus. So far, there is also no data on CoV interaction between PPE surfaces and nanoscale materials. It is believed that the interaction between viral components and nano-coating/PPE will lead to strong, nanoscale forces: effectively 'capturing' the virus. Sub-layer Up-convertor nanoparticles (UC-NP) will then permanently inactivate the virus through localized UV-radiation interaction. FIG. 1 shows the general schematic of how the coating construct captures and inactivates the virus.

DESCRIPTION OF EXEMPLARY EMBODIMENTS

In one embodiment, provided is a coating that includes a first polymer layer, wherein the first polymer layer is comprised of a cationic polymer; a second polymer layer suprajacent to the first cationic polymer layer, wherein the second polymer layer is comprised of an anionic polymer; and a third polymer layer suprajacent to the second polymer layer, wherein the third polymer layer is comprised of a cationic polymer. The first polymer layer and/or the second polymer layer, may comprise up-converting nanoparticles. In addition, the first, second and/or third polymer layer includes an oligosaccharide that binds to a virus (e.g. spike protein for the SARs-CoV-2 virus).

Up-Conversion Nanoparticles.

Figure 2:
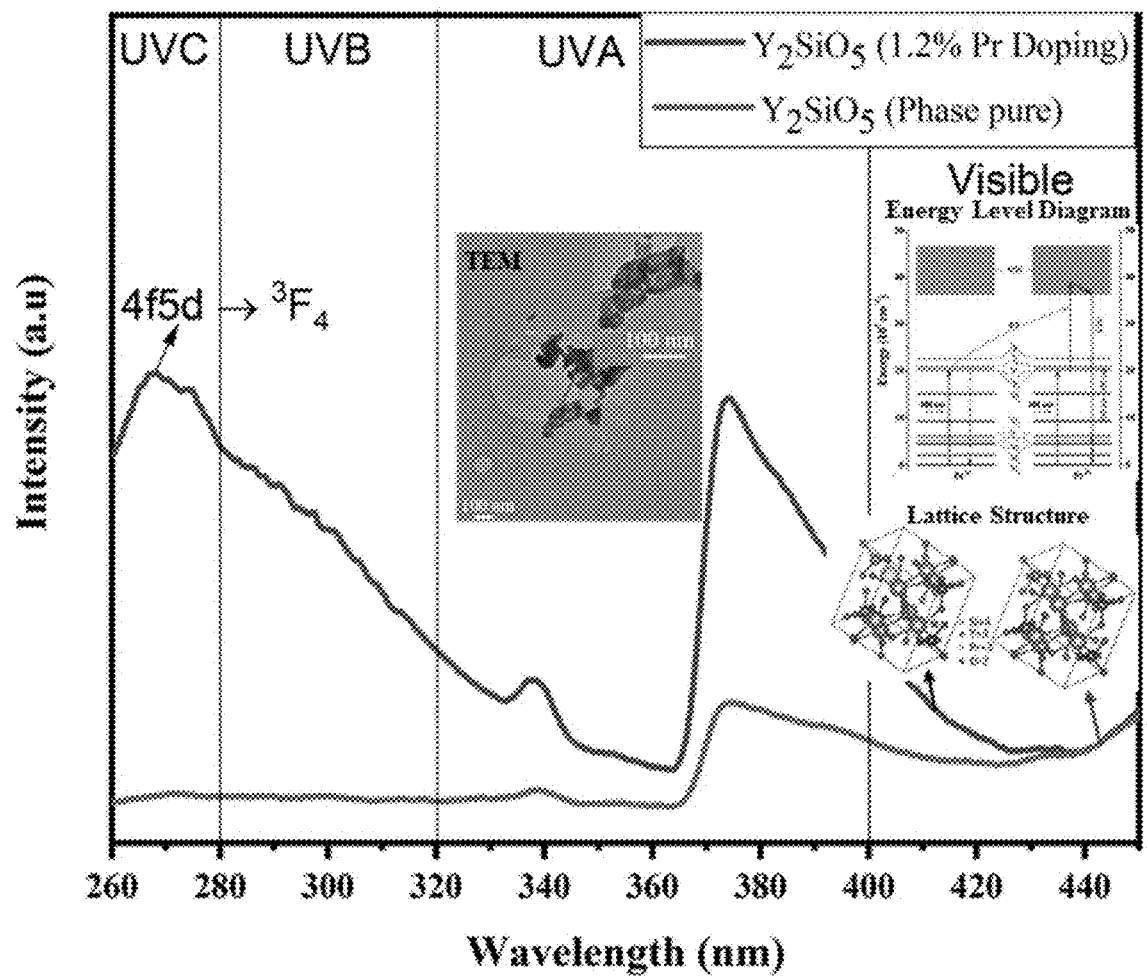
FIG. 2 shows a graph demonstrating that doped UC nanoparticles can produce UV emission in response to visible light.

For visible to UV up-conversion, a material pertaining to a luminescent Lanthanide ion with partially filled 4f sub-shells, Pr3+ (Praseodymium) is suitable and efficiency of up conversion can be enhanced by dosing with certain elements, such as Pr, Gd Nd, Pm, Sm, Eu, or Li, or a combination of any thereof. In a specific example, the lanthanide is enhanced by co-doping with Gd3+ (Gadolinium) and Li+ (Lithium). Other considerations are a suitable matrix to host the dopants, characteristics required in dopant are high tolerance for doping, chemical and thermal stability, transparency to visible radiation. Suitable candidates include fluorides ($LiYF_4$, $Lu_7O_6F_9$) and silicates ($Y_2SiO_5$, $Y_2Si_2O_7$). When using a sol-gel synthesis route, $Y_2SiO_5$ matrix is one of the candidates that may be used. FIG. 2 shows that this compound produces UV emission in response to visible light.

In one embodiment, a typical sol-gel synthesis route is utilized. Metal nitrates ($LnNO_3$ Ln: Pr, Gd, others could be: Nd, Pm, Sm, Eu: and Li) are used as precursors relative concentrations (1-2% Pr and Gd, 9-10% Li rest Y), depending upon the doping, then stoichiometric tetraethoxysilane (TEOS) is added as the silicon source and gelling agent (additional 10-20 minutes of stirring). In a particular embodiment, $Y_2SiO_5$ is doped with 1.2% Pr. The solution is heated to 50-80° C. until the formation of clear gel then it is heated at 100-120° C. for 15-17 h for xerogel formation. Xerogel is ground to powder then subjected to calcination at high temperature (900-1000° C. for 3-5 h) in the air environment followed by crushing and resuspension in ethanol via sonication (ultra sonication for 30-60 min). Finally, it is subjected to 100 nm pore size syringe filter to ensure uniform nano size (size below 100 nm).

Polymers

In one embodiment, cationic polymers that may be used to form the cationic polymer layer(s) includes chitosan, poly-l-lysine, arginine-derivatives, poly(allylamine), poly (ethylenimine) or a combination of any of the foregoing. Anionic polymers that may be used to form anionic polymers layer(s) include dodecyl sulfate, poly(acrylic acid), alginate, heparin sulfate, cellulose-derivatives, poly(styrene sulfonate) or a combination of any of the foregoing.

Coating Production

Provided herein are embodiments directed to a method of making a coating comprising a) depositing a cationic polymer solution onto a substrate to form a first cationic polymer layer onto the substrate; b) depositing an anionic polymer solution onto the first cationic polymer layer to form an anionic polymer layer; and c) depositing a cationic polymer onto the anionic polymer layer to form a second cationic polymer layer, wherein the cationic polymer solution of step (a) comprises up-converting nanoparticles and/or the anionic polymer solution of step (b) comprises up-converting nanoparticles. In a specific example, the cationic polymer solution of step (a) and/or (c) comprise an oligosaccharide or modified oligosaccharide that binds to a virus (e.g. an oligosaccharide that binds to SARS-CoV-2 spike protein). Typically, the oligosaccharide is grafted to the cationic polymer in the cationic polymer solution of step (a) or step (c) before depositing.

In one example, the up-converting nanoparticles comprise $Y_2SiO_5$ doped with Pr and Gd. The substrate can be any surface at risk of being contaminated with a virus. In a specific example the substrate is a surface of a personal protective equipment, such as a glove, face mask, or gown. In another embodiment, the substrate pertains to HVAC equipment, conduits or filters.

Ionic polymers are utilized based on charge magnitude, bio-compatibility (i.e. FDA status for use in medical products), availability (i.e. raw material and processing expenses), and environmental considerations (e.g. bio-degradability, by-products generation/character). Polymers which satisfy these and related criteria can be used in fabrication of coatings (e.g. cationic: chitosan, poly-l-lysine, arginine-derivatives, poly(allylamine), poly(ethylenimine); anionic: dodecyl sulfate, poly(acrylic acid), alginate, heparin sulfate, cellulose-derivatives, poly(styrene sulfonate)). Polymer morphology is not limited to linear chains; branched polymers are also suitable. Suitable polymers are chemically-stable (e.g. in nature, outside environment including resistance towards extensive modification through contact with common disinfectants over a range of temperatures); however, a limited bio-degradability (e.g. enzyme-mediated degradation, hydrolysis in tissue environment) may be advantageous. Grafting of an oligomeric species can be accomplished though chemical conjugation and is specific to a given polymer (e.g. binding site, reaction-type, graft density, bond strength, incorporation of intermediate linking species/agents).

The layer-by-layer design platform will be formed through a series of physical and chemical modifications over multiple steps in varied solutions. Initial preparation of a given substrate (e.g. personal protective equipment material (PPE); nitrile, polyester, polyethylene, polycarbonate, steels) may require formation of chemical groups permitting chemical conjugation of biomedically active species (e.g. nanoparticles, drugs, small molecules) or satisfactory electrostatic/physisorption of charged polymers. Substrate surface preparation may be accomplished via acid or base treatment and/or treatment with oxidizing agents. The substrate maybe washed thoroughly with de-ionized water before further modification. From here, the surface may be modified as stated above via reaction specific chemistry (e.g. chemical linker-mediated conjugation of nanoparticles to PPE surface). Formation of the layer-by-layer film is performed via a series of immersions. Immersion can be accomplished via dip coating, with immersion and retraction performed at controlled rates in consideration of capillary/cohesive forces at solution surfaces. Firstly, the material will be immersed in an aqueous solution of cationic polymers, with or without previous chemical modification, over a period of not less than 5 minutes. Subsequently, the material will be immersed in de-ionized water to remove ad-layers of material for no less than 5 minutes. Then, the material will be immersed in a solution of cationic polymers. Cationic polymer containing solution may also contain additional dispersed or interacting functional agents (e.g. nanoparticles, drugs, small molecules) to be incorporated in the layer by layer film. The material will again be immersed in fresh de-ionized water to remove ad-layer species. The detailed procedure of alternating immersions, and washings, will be repeated to a desired extent (e.g. to a desired film thickness). However, the terminal layer (i.e. application environment interfacing layer) will necessarily be the virus-interacting oligomer modified layer to allow direct interface with virus.

The cationic layer will be grafted with oligosaccharides (optionally modified), chosen to bind strongly to unique/specific virus surface features (e.g., N-acetyl neuraminic acid and its derivatives binding to SARS-CoV2 spike protein), thereby mediating capture of the virus (with the choice of oligomeric species allowing generalization to a given virus). Natural light (excitation) to UV (local emission) up-converting nanoparticles (UCNP, novel rare earth doped silicate composition generating high-efficacy, anti-viral UV-C and B emission) are seeded into the anionic layer and will mediate the inactivation ('killing') of the bound virus species.

Other oligosaccharides that may be used in the polymer coatings include glycosaminoglycans and N-glycans, such as but not limited to N-acetyl glucosamine, N-acetyl galactosamine, sialic acid (or its derivatives), or heparan sulfate. Typically, glycans contain 5-12 sugar units, 1-2 branches, and, optionally, a fucose unit or sialic acid unit, such as those commercially available from GlyTech, Inc. (product nos GT-25001, GT-25002, GT-25006, GT-25010, GT-25016, GT-25022, GT25023, GT-25024, GT-25132, GT-25133, GT-25137, GT-25141, GT-25144, GT-147, GT-25153, GT-25154, GT-25155, GT-25182, GT-25183, GT-25184, or GT-25187). Information of other glycans and saccharide molecules that bind to viruses is provided in Glycan Engagement by Viruses: Receptor Switches and Specificity, Luisa J. Ströh and Thilo Stehle, *Annual Review of Virology* 2014 1:1, 285-306, incorporated by reference. Information of heparan sulfate oligosaccharides is provided in Binding of the SARS-CoV-2 Spike Protein to Glycans, Wei Hao, Bo Ma, Ziheng Li, Xiaoyu Wang, Xiaopan Gao, Yaohao Li, Bo Qin, Shiying Sh ang, Sheng Cui, Zhongping Tan, *bioRxiv* 2020.05.17.100537, incorporated by reference.

$Y_2SiO_5$ (1% Pr, 1% Gd) and $Y_2SiO_5$ (1% Pr, 1% Gd, 10% Li) formulations have shown good test results. $Y_2SiO_5$ (1% Pr, 1% Gd) has reduced active viral load from $4*10^4$ to 9.28 (more than 90% decrease in active viral load) and $Y_2SiO_5$ (1% Pr, 1% Gd, 10% Li) has reduced viral load from $4*10^4$ to 0 (100%) in an hour of exposure to white light. Furthermore, binding of the virus to the coating surface layer can reduce interaction with sub-layers and allow the release of inactivated bound virus: producing a fresh surface to allow further virus capture. The 'capture and kill' system, detailed in this disclosure, combines the general anti-viral activity of UV-C and B generation with the specificity of an oligosaccharide (glycan) bio-receptor virus recognition. In this way, the system can mediate anti-viral activity towards unique species or produce a 'broad spectrum' approach through modulation of a bio-recognition component. Further, the use of oligosaccharide species exists as a substantial improvement over traditional recognition elements, such as antibodies or aptamers, which are strongly susceptible to degradation (e.g. from light, temperature change, solution tonicity, pH). The detailed platform also benefits from ease of fabrication and conformation to materials/surfaces with unique/ complex topology.

In alternative embodiments, one or more layers of a created coating may also include nanoparticles loaded with an antiviral agent. The antiviral agent is released over time or in response to contact, pressure change, temperature change, moisture change, pH change and the like. In a specific example, the antiviral agent comprises chloroquine and/or hydroxychloroquine. The loaded nanoparticle may include a hollow center into which the anti-viral agent is disposed. Typically the loaded nanoparticles are mixed with a given polymer solution, cationic and/or anionic, before deposition onto a substrate.

EXAMPLES

Example 1: Development of UC-NPs and Direct Interaction with CoV Model Species Rationale:

Most studies addressing PPE have focused on virus contamination on artificial surfaces, [14-16] but not on inactivation in the context of PPE. Prior work has shown that CoVs and other RNA viruses are very sensitive to exposure to UV light. [17, 18] Thus, we believe that UC-NP embedded in nanocoated PPE in combination with light provides a novel mechanism to both capture virus particles and also rapidly inactivate them. It is also believed that design of a nanomaterial which can upconvert visible light to UV radiation locally disrupts CoV upon interaction. Lanthanidedoped nano $Y_2SiO_5$ (Doping: Pr, Gd) with versatile visible to UV up-conversion properties [19-27] has shown antimicrobial properties [19, 20] is a suitable candidate. UV up-conversion from NIR (near infrared) radiation is used [28-31] for cancer cell imaging and other therapeutic applications. A study of photodynamic inactivation of Dengue virus (>50% reduction) has been done [28] although radiation used was NIR but the localized emission (Visible) mechanism remains the same.

Synthesis UC-NPs and Optimization for Natural Light Absorption, UV Emission.

A facile scalable sol-gel based synthesis of $Y_2SiO_5$(Doping: 1-2% Pr and/or Gd) is utilized. Metal nitrates are used as precursors with relative concentrations (1-2% Pr and Gd, rest Y) depending upon the doping, then stoichiometric tetraethoxysilane (TEOS) is added as silicon source and gelling agent (10 minutes of stirring). The solution is heated to 70° C. until formation of clear gel then it is heated at 100° C. for 17 h for xerogel formation. Xerogel is ground to powder then subjected to calcination in the air followed by crushing and resuspension in ethanol via sonication (ultra-sonication: 1-2 h). Finally, it is subjected to 100 nm pore size syringe filter to ensure uniform nano size (size below 100 nm).

Nano Characterization of UC-NP Formulations.

X-ray diffraction (XRD), X-ray photoelectron spectroscopy (XPS), Scanning electron microscopy (SEM) and Transmission Electron microscopy (TEM) is conducted to determine the constituent phases, size, surface chemistry and morphologies of UC-NPs.

UC-NP UV Dosimetry and Radiative Transfer Characterization:

Fluorescence spectroscopy (emission (UV range) and excitation scans (visible range)) are used to confirm upconversion properties.

Degradation of H2O2-Monoazo Dyes by UC-NPs.

Control and UC-NPs (5-30%) samples with H2O2-Monoazo dyes are exposed to white light followed by assessment of absorption value using UV-Vis spectroscopy then compared with reported UV dye degradation results to estimate up conversion [33].

Testing of UC-NP Formulations' Inactivation of CoV Under Controlled Irradiation.

There are three parameters to test—NP composition, Virus dose and time of light exposure. UC-NP of various composition is spiked with increasing amounts of CoV (0, 102, 104 or 106 PFU). UC-NP virus samples is exposed to light from lamp source of fixed emission bandwidth and intensity, leading to UV light emission for varying times (0, 10, 20, 30 min) and then assayed for remaining infectivity by viral assay. Viral genomes are assayed by RT-PCR. Initial studies will use solution samples due to ability to make rapid progress, with next steps involving nanocoated glass slips and/or nitrile gloves. We expect to see time-dependent loss of infectivity in the samples exposed to UV light, with no detectable infectivity seen by 30 min of exposure.

Example 2: Formulate LBL Nanocoating on Nitrile Rubber or Glass Substrate

Rational:

COVID-19 pandemic presents multiple challenges, from a scientific and technological standpoint in novel studies of nanomaterials to contain virus contamination. Special interest is currently being paid to materials which can inactivate the virus before causing human infection. A multi-layer, nanocoating via layer-by-layer deposition (LBL) of cationic and anionic polymers, as well as UC-NPs, developed in Example 1 above, can function to model general nanomaterial-virus protein interactions for future studies/functional PPE products. Further, grafting of carefully selected oligosaccharides to the cationic polymer can allow a CoV-specific interaction. The interaction between spike protein (SPs) and nano-coating outer layer leads to strong, nanoscale forces: effectively 'capturing' the virus. Further, cationic polymer binding to the virus disrupts bonding between the surface and sub-surface layers: allowing release of the tightly bound polymer-virus complex and regeneration of the active surface towards further virus capture.

Determine Optimal Oligosaccharide Chemical Structure for S Protein Binding.

Different oligosaccharides are initially chosen, based on S protein surface composition (determined from NIH protein database). From here, bond strength between S protein and candidate oligosaccharides is assessed via column affinity chromatography (chemical binding of candidate molecules to chromatography beads stationary phase followed by elution of S protein containing phase). Finally, elution time and virus titer are assayed through qPCR. Alternatively, oligosaccharides may be assayed for relative binding affinity through an ELISA-type assay, as an inhibition assay between S protein and ACE2 binding, with IC50 values determined and compared. From here, the oligosaccharide is grafted to the cationic polymer. Moore et al., ACS Infect Dis 2021, 7(2)254-263 provide examples of antiviral oligosaccharides, and is incorporated herein by reference. In a specific embodiment, an FDA-approved, biocompatible cationic polymer (e.g. chitosan) is used as a starting material. An oligosaccharide species, chosen to possess strong bond affinity/complementarity to novel CoV S glycoprotein, is grafted to the polymer using functional groups/sites such as via click chemistry. Conjugation is characterized confirmed via Fourier transform infrared spectroscopy and XPS spectroscopies.

Grafting glycan species to a cationic polymer may be accomplished through reaction at varied functional group sites, leading to unique (N- or O-) linkages to defined chemical sites on the polymer. As an example, N-acetyl neuraminic acid may be grafted to chitosan through reaction between the carboxylic acid of N-acetyl neuraminic acid and an amine of chitosan via an EDC/sulfo-NHS conjugation chemistry. Specifically, 20 mg N-acetyl neuraminic acid is initially dissolved from a powder into 10 mL of a pH 6.0 buffer (0.1 M MES (2-(N-morpholino)ethanesulfonic acid) and 0.5 M sodium chloride). EDC.HCl (ethyl(dimethylaminopropyl) carbodiimide hydrogen chloride) to 4 mM and sulfo-NHS (N-hydroxysulfosuccinimide) to 10 mM are added, followed by mechanical agitation (vortexing) until complete reactant dissolution. The reaction is allowed to occur for approximately 15 minutes, followed by de-activation of residual EDC.HCl via β-mercaptoethanol addition. In a fresh 10 mL volume of MES buffer, de-acetylated chitosan is added and stirred until completely dissolved. From here, the two prepared solutions are combined, stirred for 3 hrs, and dialyzed against a desired solution/solvent (for purification or exchange to an alternative dispersing medium). Optionally, the formed conjugate may be subsequently lyophilized.

Fabricate and Characterize LBL+UC-NP Nanocoating Structure.

LBL nanocoating is fabricated from separate cationic and anionic polymer solutions (in dH2O). Firstly, the substrate glass or nitrile rubber is 'activated' towards conjugation through the installation of de-protonated hydroxyl groups. UC-NPs are functionalized with amine groups through reaction between surface hydroxyls and 1-ethyl-3-(3-dimethylaminorpropyl) carbodiimide (EDC). Subsequently, these amine functionalized particles are then bonded to the substrate by peptide bonding mediated by epichlorohydrin treatment. From here, the substrate may be alternately immersed (for a fixed number of cycles), via dip coater, into the polycationic and anionic (e.g. heparin sulfate; additionally containing free, un-modified UC-NPs) solutions. The nanocoatings structure is characterized by SEM and cryo-TEM.

Any changes in virus inactivation may arise from a number of issues. A monolayer model composed of a single cationic layer on the substrate can be used to determine if virus binding is a contributing issue by titrating with virus and washing. From here, SEM can be performed and the number of bound viruses per field of view determined. Alternatively, the virus-bound substrate can be immersed in a lysate buffer, and the genomic RNA quantified via qPCR. If UC-NPs are the limiting factor in performance, their surfaces can be modified with oligosaccharides to decrease the separation between virus particles and UC-NPs: ensuring high radiative transfer. Alternatively, a hollow polymeric nanoparticle filled with CoVID-19-active hydroxychloroquine can be incorporated in addition or substitution of the UC-NPs, without further modification of the nanocoating composition.

The teachings of any references cited herein are incorporated in their entirety to the extent not inconsistent with the present disclosure. Although the present invention has been described in considerable detail with reference to certain preferred versions thereof, other versions are possible. Therefore, the spirit and scope of the appended claims should not be limited to the description of the preferred versions contained herein. The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or"step for" performing a specific function, is not to be interpreted as a "means" or "step" clause as specified in 35 U.S.C § 112, sixth paragraph. In particular, the use of 'step of in the claims herein is not intended to invoke the provisions of 35 U.S.C § 112, sixth paragraph.

What is claimed is:

1. A coating comprising
  a first polymer layer, wherein the first polymer layer is comprised of a cationic polymer;
  a second polymer layer suprajacent to the first cationic polymer layer, wherein the second polymer layer is comprised of an anionic polymer; and
  a third polymer layer suprajacent to the second polymer layer, wherein the third polymer layer is comprised of a cationic polymer;
  wherein the first, second or third polymer layers comprise up-converting nanoparticles; and wherein the first, second or third polymer layer comprises an oligosaccharide that binds to a virus.

2. The coating of claim 1, wherein the oligosaccharide binds to SARS-CoV-2 spike protein.

3. The coating of claim 1, wherein the up-converting nanoparticles comprise $Y_2SiO_5$ doped with Pr and/or Gd.

4. The coating of claim 1, wherein the cationic polymer of the first and/or third polymer layer comprises chitosan, poly-l-lysine, arginine-derivatives, poly(allylamine), poly (ethylenimine) or a combination of any of the foregoing.

5. The coating of claim 1, wherein the anionic polymer of second polymer layer comprises dodecyl sulfate, poly (acrylic acid), alginate, heparin sulfate, cellulose-derivatives, poly(styrene sulfonate) or a combination of any of the foregoing.

6. A method of making a coating comprising a) depositing a cationic polymer solution onto a substrate to form a first cationic polymer layer onto the substrate; b) depositing an anionic polymer solution onto the first cationic polymer layer to form an anionic polymer layer; and c) depositing a cationic polymer solution onto the anionic polymer layer to form a second cationic polymer layer, wherein the cationic polymer solution of step (a) comprises up-converting nanoparticles and optionally, the anionic polymer solution of step (b) comprises up-converting nanoparticles, wherein cationic polymer solution of step (a) and/or (c) and/or the anionic polymer solution of step (b) comprise an oligosaccharide that binds to a virus.

7. The method of claim 6, wherein the oligosaccharide is grafted to the cationic polymer in the cationic polymer solution of step (a) or step (c) before depositing.

8. The method of claim 6, wherein the oligosaccharide binds to SARS-CoV-2 spike protein.

9. The method of claim 6, wherein the up-converting nanoparticles comprise $Y_2SiO_5$ doped with Pr, Gd Nd, Pm, Sm, Eu, or Li, or a combination of any thereof.

10. The method of claim 9, wherein the up-converting nanoparticles are doped with Pr and/or Gd.

11. The method of claim 6, wherein the cationic polymer of the first and/or third polymer layer comprises chitosan, poly-l-lysine, arginine-derivatives, poly(allylamine), poly(ethylenimine) or a combination of any of the foregoing.

12. The method of claim 6, wherein the anionic polymer of second polymer layer comprises dodecyl sulfate, poly(acrylic acid), alginate, heparin sulfate, cellulose-derivatives, poly(styrene sulfonate) or a combination of any of the foregoing.

13. The method of claim 6, wherein the up-converting nanoparticles are produced by mixing $PrNO3$ and $GdNO3$ with tetraethoxysilane to form a mixture and then heating the mixture to form a gel.

14. The method of claim 13, wherein the gel is a xerogel, and the method further comprises grinding the gel into particles and filtering the particles.

15. The method of claim 6, wherein the substrate comprises a surface of a personal protective equipment (PPE) or an air filter.

16. The coating of claim 5, wherein the first, second or third polymer layers further comprise a loaded nanoparticle, wherein the loaded nanoparticle is loaded with an antiviral agent.

17. The coating of claim 16, wherein the antiviral agent is released over time or in response to contact, pressure change, temperature change, moisture change, pH change and the like.

18. The coating of claim 16 wherein the antiviral agent comprises chloroquine and/or hydroxychloroquine.

19. The coating of claim 16, wherein the loaded nanoparticle comprises a hollow center into which the anti-viral agent is disposed.

* * * * *